United States Patent [19]

Sinka et al.

[11] 4,382,135

[45] May 3, 1983

[54] RADIATION-HARDENABLE DILUENTS

[75] Inventors: Joseph V. Sinka, Mendham; Francis A. Higbie, Bound Brook; Robert A. LieBerman, Hopatcong, all of N.J.

[73] Assignee: Diamond Shamrock Corporation, Dallas, Tex.

[21] Appl. No.: 250,058

[22] Filed: Apr. 1, 1981

[51] Int. Cl.³ .................. C07C 69/54; C08F 226/00
[52] U.S. Cl. ............................... 526/301; 526/320; 526/323.2; 204/159.19; 204/159.23; 560/224
[58] Field of Search ............ 560/224; 526/320, 323.2, 526/301; 204/159.19, 159.23

[56] References Cited

U.S. PATENT DOCUMENTS

| | | |
|---|---|---|
| 3,594,410 | 7/1971 | Cohen et al. |
| 3,769,336 | 10/1973 | Lee, Jr. .................. 560/224 |
| 3,857,822 | 12/1974 | Frass . |
| 4,025,548 | 5/1977 | Huemmer et al. .................. 560/224 |
| 4,058,443 | 11/1977 | Murata et al. . |
| 4,088,498 | 5/1978 | Faust . |
| 4,177,074 | 12/1979 | Proskow . |
| 4,179,478 | 12/1979 | Rosenkranz et al. . |
| 4,180,474 | 12/1979 | Schuster et al. . |
| 4,205,025 | 6/1980 | Vrancken et al. ............. 204/159.16 |
| 4,302,381 | 11/1981 | Omura et al. .................. 560/224 |

*Primary Examiner*—Natalie Trousof
*Assistant Examiner*—L. Hendriksen
*Attorney, Agent, or Firm*—Neal T. Levin

[57] ABSTRACT

Radiation curable diluents have been developed which are acrylic acid esters of alkoxylated 1,6-hexanediol, neopentyl glycol and tripropylene glycol, each having a relatively low degree of alkoxylation. Examples are diacrylates of adducts of neopentyl glycol with two moles, four moles and six moles, respectively, of ethylene oxide and with two moles and four moles, respectively, of propylene oxide.

16 Claims, No Drawings

RADIATION-HARDENABLE DILUENTS

BACKGROUND OF THE INVENTION

1. Field of the Invention

This invention relates to radiation-hardenable diluents which are based on acrylic acid esters of alkoxylated 1,6-hexane diol; neopentyl glycol and tripropylene glycol each having a relatively low degree of alkoxylation for use in radiation-hardenable compositions which contain oligomers (also known as binders).

2. Description of the Prior Art

Radiation-hardenable compositions, particularly for coating applications are known in the art. In view of the restrictions on solvent content in the atmosphere, increasing efforts have been made to provide completely polymerizable systems which do not contain any volatile components, but instead consist of constituents which form either the whole or a part of the hardened film itself. Monomers which are useful for this purpose are known. For example, see U.S. Pat. Nos.:

3,594,410—Cohen et al—July 20, 1971
3,857,822—Frass—Dec. 31, 1974
4,058,443—Murata et al—Nov. 15, 1977
4,088,498—Faust—May 9, 1978
4,177,074—Proskow—Dec. 4, 1979
4,179,478—Rosenkranz et al—Dec. 18, 1979
4,180,474—Schuster et al—Dec. 25, 1979.

Among the diluents disclosed are polyacrylates of polyhydric alcohols such as polyethylene glycol, glycerol, neopentyl glycol, trimethylolpropane, pentaerythritol, etc., and polyacrylates of polyhydric alcohols reacted with alkylene oxide such as with ethylene oxide, i.e., addition products of one mole of trimethylol propane and 2.5 to 4 moles of ethylene oxide. However, it is pointed out in the context of U.S. Pat. No. 4,088,498 that compounds free from ether linkages are preferred.

The selection and proportion of useful diluents is very important. That is, the presence and proportion of these esters of acrylic acid as diluents in the radiation-hardenable composition influence the parameters of the system to be cured as well as the hardened film, for example, viscosity, cure rate, percent elongation, tensile strength, solvent resistance, scuff resistance and adhesion. For example, it is known that hexane diol diacrylate very effectively reduces viscosity of a resin, but at the same time has an extremely adverse effect upon properties of the oligomer. On the other hand, it is known that trimethylolpropane triacrylate has only a slight effect upon the properties of an oligomer, but is unable sufficiently to reduce the viscosity and at the same time imparts greater hardness but also poorer adhesion to the coating on account of the relatively high crosslinking density. Further, it has been found that certain diluents are irritating when handled. This, therefore, renders unacceptable certain diluents even though other properties are acceptable.

SUMMARY OF THE INVENTION

Outstanding radiation-hardenable diluents for use with radiation-hardenable compositions which contain oligomers having reduced irritation and improved cure rate and responsible for improved percent elongation, tensile strength, solvent resistance, scuff resistance and adhesion are those which are acrylic acid esters of alkoxylated 1,6-hexanediol; neopentyl glycol and tripropylene glycol, each having a relatively low degree of alkoxylation.

DESCRIPTION OF THE PREFERRED EMBODIMENTS

Diluents

More specifically, the diluents are diacrylates of the reaction products of a diol selected from the group consisting of 1,6-hexane diol, neopentyl glycol and tripropylene glycol with from about 2 to about 6 moles of one or a mixture of an alkylene oxide selected from the group consisting of ethylene oxide and propylene oxide.

Examples of diluents characterized by having the aforementioned properties and responsible for improvements in the hardened coating are:

the diacrylate of the adduct of 1,6-hexane diol and 3.7 moles of propylene oxide the diacrylate of the adduct of 1,6-hexane diol and 2 moles of ethylene oxide the diacrylate of the adduct of neopentyl glycol and 2 moles of ethylene oxide the diacrylate of the adduct of neopentyl glycol and 4 moles of ethylene oxide the diacrylate of the adduct of neopentyl glycol and 6 moles of ethylene oxide the diacrylate of the adduct of neopentyl glycol and 2 moles of propylene oxide the diacrylate of the adduct of neopentyl glycol and 4 moles of propylene oxide the diacrylate of the adduct of tripropylene glycol and 2 moles of ethylene oxide the diacrylate of the adduct of tripropylene glycol and 4 moles of ethylene oxide.

Other examples are mixed ethylene oxide, propylene oxide condensates of the diols.

The diluents can be prepared in two steps as shown below:

A. Preparation of the Alkylene Oxide Condensates

The specified monomer base is charged to a reaction flask equipped with stirrer, thermometer and gas inlet pipes and heated to melt product if necessary. Once product is uniform, it is heated to 125°–140° C. where the catalyst, caustic potash, is added. Concentration of catalyst ranges from 0.1–0.3 percent by weight of charge, depending whether ethoxylation or propoxylation is conducted and the type of chain structure. Branched chains and products using propylene oxide usually require higher levels of catalyst. To this mixture, ethylene oxide, propylene oxide or mixture of both is added slowly until the product obtains final specifications. In some instances, the product must first be stripped under vacuum before alkoxylation to remove any water in base monomer.

B. Preparation of the Acrylate Esters of the Alkylene Oxide Condensates

The alkoxylated monomer is azeotropically esterified with 20–55 percent by weight of the alkoxylated monomer, of acrylic acid and 1.5–2.5 percent by weight of the alkoxylated monomer, of p-toluene sulfonic acid in the presence of 20–45 percent by weight of the total charge, of toluene. Concentration of ingredients varies depending on degree of esterification desired (mono or di) and on the particular reactivity of the alkoxylated monomer. Inhibitors such as methylene blue, phenothiazine, cuprous oxide, copper powder, nitrobenzene, and triphenyl phosphite, generally in amounts of from about 0.05% to about 1.0% by weight of the total charge are added during the reaction to inhibit polymerization of product. The reaction is contained until no further water is isolated. The product is then washed and neutralized with sodium carbonate. Paramethoxyphenol is added (700 ppm–3500 ppm) and the toluene distilled off in vacuo (final pressure is about 28 inches of mercury, final temperature of reaction is about 100° C.). The product is filtered for clarity.

The radiation-hardenable compositions which contain the diluent and oligomer, may be hardened by means of high-energy radiation, such as UV-light, electron beams, gamma rays etc., preferably by UV-light.

In cases where polymerization is carried out with UV-light, the photoinitiator used may be any one of the compounds normally used for this purpose, for example, benzophenone and, quite generally, aromatic keto compounds derived from benzophenone, such as alkyl benzophenones, halogen-methylated benzophenones. Michler's ketone, anthrone and halogenated benzophenones. Other effective photoinitiators are anthraquinone and many of its derivatives, for example $\beta$-methyl anthraquinone, tert.-butyl anthraquinone and carboxylic acid esters, chlorosulphonated xanthones and thioxanthones and also oxime esters. Other useful photoinitiators are benzoin ethers such as benzoin methyl ether, benzoin ethyl ether, benzoin butyl ether, benzil ketals such as benzil and acetophenone derivatives such as diethoxyacetophenone.

The above-mentioned photoinitiators may be used in quantities of from 0.2 to 10 percent by weight, preferably in quantities of from 1 to 5 percent by weight based on the total composition. They may be used either individually or in combination with one another.

Advantageous additives which can produce a further increase in reactivity are certain tertiary amines such as triethylamine, aminoacrylates such as 2 (n-butoxy) ethyl 4-dimethylamino benzoate and amine synergist compounds. Additions of phosphines or thioethers are similarly active. The abovementioned substances are preferably used in quantities of from 0 to 20 percent by weight, based on the total composition.

Like any system capable of vinyl polymerization, the radiation-hardenable resin compositions have present polymerization inhibitors in order to obtain high stability in storage. Suitable compounds are phenols, for example, hydroquinone, toluhydroquinone, di-tert.-butyl-p-cresol, hydroquinone monomethyl ether and also phenothiazine or copper compounds. The quantity to be added is determined by the required degree of stabilization and also by the acceptable losses of reactivity which are frequently incurred by the addition of stabilizers. The type and optimum quantity of stabilizer must be determined by concentration tests to be carried out from case to case with varying concentrations of stabilizer. The stabilizers are generally added in quantities of from 0.001 to 0.5 percent by weight, based on the total composition. Examples of oligomers with which the diluents are used are reaction products of at least one polyepoxide containing more than one 1,2-epoxide group per molecule and acrylic or methacrylic acid or mixtures thereof, about 0.6 to 1 mole of carboxyl groups having been used to one epoxide group. The polyepoxides may be pre-extended (polyfunctional compounds) or modified (monofunctional compounds) with ammonia, aliphatic or cycloaliphatic primary or secondary amine, with hydrogen sulphide, aliphatic, cycloaliphatic, aromatic or aliphatic dithiols or polythiols, with dicarboxylic acid and polycarboxylic acids, from 0.01 to 0.6 NH or SH or COOH equivalents per one epoxide equivalent. The reaction products described above may optionally have been modified with isocyanates. Also epoxidized natural oil acrylates such as epoxidized linseed oil acrylate and epoxidized soya acrylate may be used.

The radiation-hardenable compositions also include unsaturated polyesters which contain radiation-hardenable saturated and unsaturated carboxylic acids, such as maleic acid, fumaric acid and adipic acid in co-condensed form such as a copolymer of adipic and acrylic acid.

Reaction products of diisocyanates and polysiocyanates with hydroxy alkyl acrylates and methacrylates can be used as well as other urethanes containing acrylic and methyacrylic acid units. An example is a toluene diisocyanate based acrylate compound. Also other useful oligomers are based on bisphenol A type compounds such as the diglycidyl ether of bisphenol A diacrylate.

The diluents or mixtures thereof according to the invention may be present in the radiation-hardenable mixtures in a proportion of from 5 to 80 percent by weight and preferably in a proportion of from 10 to 70% by weight based on the total mixture.

The compositions produced with the diluents according to the invention are suitable for use as coating and impregnating compositions for wood, paper, cardboard, plastics, leather, metals, textiles and ceramic materials. These compositions may also be used as binders for printing inks, photoresists for the production of screen printing forms, screen printing compositions, adhesives for pressure sensitive tapes, decals and laminates.

Test Methods

The test methods used in collecting the data herein are described below. Surface tension and the Draize (irritation) test were carried out with the diluent while solvent resistance, scuff and adhesion were carried out upon cured coatings of the diluent upon paper, aluminum and tin substrates. Determinations of percent elongation and tensile strength were made upon cured compositions containing the diluent and oligomer (binder).

Adhesion

Follow the cross hatched method using #600 cellotape giving 40 pound per linear inch pull up where the degree of adhesion is a measure of the amount of film left on substrate after the tape is removed from the etched area.
E=Excellent—no removal of film
G=Good—slight removal of film along etched lines
F=Fair—removal of film on etched area
P=Poor—removal of film.

Scuff Resistance

An arbitrary measurement using a fingernail and is measured by the resistance to tearing of the coating. This is done by running a fingernail at a 90° angle to the film several times.
G=Good—no marking of film
F=Fair—slight marking
P=Poor—penetration and tearing of film.

Solvent Resistance

Use methylethyl ketone as test solvent. Numbers signify the amount of rubs (1 rub=one back and forth motion) with a cotton swab soaked with methylethyl ketone required to etch and penetrate film.

Percent Elongation and Tensile Strength

Wet films of 2.52 mils are prepared using a number 28 RDS rod. Coatings are then cured at 100 ft./min. until a non-tacky coating is obtained.

Films 4 inches long and ⅜ inch wide are then cut and removed from substrate. Average film thickness is then determined using a micrometer.

Samples are then placed in an Instron Universal Tester, Model TTD using 200 pound cell, with clamp distances being two inches. Samples are run and measurements for tensile strength and percent elongation are calculated from chart.

Surface Tension

Using a Rosano Surface Tensiometer, the instrument is calibrated with reagent grade toluene at 25° C. Samples are then measured at 25° C. until a constant value is obtained.

Cure Rate

Using a Fusion Systems ultraviolet curing machine Model No. F440, samples are cured with a 300 watt-/inch bulb suspended two inches from substrate at 100 feet/minute line speed. Samples are repeatedly passed through machine until a non-tacky film is obtained.

Degree of Irritation

Determined by the Draize Test. The higher the number, the greater the irritation and hence the less desirable the diluent.

The protocol used was as follows:

Purpose

To determine the potential for skin irritation produced when the test article is applied to rabbit skin in accordance with HSLA regulations as cited in 16 CFR 1500.41.

Choice of Test System

The albino rabbit has been shown to be a good model for skin irritation studies and is required by the regulations cited above.

Procedure

Animals: Six adult New Zealand white rabbits, purchased from an approved USDA supplier and weighing between 2 and 4 kg initially, were used in this study. All animals were acclimated for a period of 5 to 10 days and were examined with respect to their general health and suitability as test animals. The rabbits were housed individually in wire-mesh cages and Laboratory Rabbit Formula and water were offered ad libitum.

Method

Not more than 24-hours prior to the dermal applications, the back and flanks of each rabbit was clipped free of fur with a commercial electric clipper and a Number 40 blade. The animals were then returned to their cages.

On the day of testing, and just prior to the applications of the test article, abrasion of the skin was performed on the right dorsal side of each rabbit (6) with the point of a 23 gauge, disposable hypodermic needle. The abrasions were minor incisions through the stratum corneum and not sufficiently deep to disturb the derma or to produce bleeding. The left dorsal side was left intact.

Exactly 0.5 ml., if liquid, or 0.5 gram, if solid (moistened with 0.5 ml of physiological saline) of the test article, was applied to each of two sites, one on abraded skin, and the other on intact skin of each rabbit. The test sites were occluded with a one-inch by one-inch square gauze patch, two single layers thick. The patches were secured in place with masking tape. The trunk of each animal was then wrapped with an occlusive binder which consisted of a layer of plastic wrap, a protective cloth and a Stockingnette ® sleeve, all securely held in place with masking tape. The exposure period was 24 hours.

Observation

At the end of 24 hours, the occlusive binders and patches were removed. The sites were gently wiped with clean gauze to remove as much non-absorbed test material as possible. One-half hour after unwrapping, the skin sites were examined and scored separately for both erythema and edema on a graded scale of 0 to 4 according to the skin reaction code below. After 72 hours the sites were again examined and rescored.

Daily observations were not recorded, however, any extraordinary findings, dermal or toxicological, were noted.

Calculation

In evaluating the average irritation, scores for individual intact and abraded sites were recorded separately for each of the two scoring time intervals. A subtotal for erythema and eschar formation was added to a subtotal for edema, then divided by 4 to yield the individual animal score. The mean of the six scores was then calculated and represented the mean primary irritation score, also referred to as PII (Primary Irritation Index).

Skin Reaction Code

|  | Value |
| --- | --- |
| Erythema and Eschar Formation: | |
| No erythema | 0 |
| Very slight erythema (barely perceptible) | 1 |
| Well-defined erythema | 2 |
| Moderate to severe erythema | 3 |
| Severe erythema (beet redness) to slight eschar formations (injuries in depth) | 4 |
| Edema Formation: | |
| No edema | 0 |
| Very slight edema (barely perceptible) | 1 |
| Slight edema (edges of area well defined by definite raising) | 2 |
| Moderate edema (raised approximately 1 mm.) | 3 |
| Severe edema (raised more than 1 mm. and extended beyond the area of exposure) | 4 |

For the foregoing, see Draize, John H., Woodard, Geoffrey, and Calvery, Herbert O., "Methods for the Study of Irritation and Toxicity of Substances Applied Topically to the Skin and Mucous Membranes", *J. Pharm. & Exp. Ther.* 82, 337 (1944).

Preparation of Films or Coatings of Monomer (Diluent)

Formulations of monomer (diluent) with photoinitiator are prepared and applied with a RDS coating rod No. 3 (giving a wet film thickness of 0.27 mils) to the substrate. These coatings are then passed through a Fusion Systems ultraviolet curing machine Model No. F440 equipped with a 300 watt/inch bulb suspended 2 inches from substrate at 100 feet/minute line speed until the coatings are cured and as tack free as possible. Cured coatings are then tested for performance within one hour after curing.

Formulation for diluent used in the various tests was:

| Component | % by Weight |
|---|---|
| Diluent (monomer) | 96 |
| 2,2-dimethyl-2-phenyl acetophenone (photoinitiator) | 4 |

Preparation of Films of Compositions Containing Monomer (Diluent) and Oligomer

Formulations of monomer (diluent), oligomer and photoinitiator are prepared by simple mixing, applied neat to a substrate and cured by the procedure described above.

Formulation for diluent-binder (oligomer) was:

| Component | % by Weight |
|---|---|
| Acrylated urethane, the urethane base being a short chain aromatic toluene diisocyanate compound(oligomer CMD 6700-Celanese Plastics and Specialties) | 48 |
| Diluent (monomer) | 48 |
| 2-Hydroxyl-2-methyl-1-phenyl propan-1-one (photoinitiator) | 4 |

Substrates used were:
Paper—Opacity test panel form 013, from Morest Corp.
Aluminum and tinplated steel panels from Q Panel Corp.

For a fuller understanding of this invention, reference may be made to the following examples. These examples are given merely to illustrate the invention and are not to be construed in a limiting sense.

EXAMPLE I (A) Preparation of ethoxylated neopentyl glycol with a degree of ethoxylation of 2.

54.09 grams of neopentyl glycol were charged to a reaction flask equipped with stirrer, thermometer and gas inlet pipes and heated to 130° C. Then 0.2 gram of caustic potash was added. Then 45.71 grams of ethylene oxide were added slowly. On completion, the product was stripped and cooled. The final product obtained had a maximum gardner of 2, and a hydroxyl number of 556–560.

(B) Preparation of the diacrylate of the ethoxylated neopentyl glycol obtained in part A above.

64.3 grams of the ethoxylated neopentyl glycol with a degree of ethoxylation of 2 obtained in accordance with part A above were azeotropically esterified with 51 grams of acrylic acid in 42.8 grams of toluene in the presence of 2.1 grams of p-toluene sulphonic acid and inhibitors, until no more water could be isolated. On completion, the product was washed, neutralized with sodium carbonate, 1000 parts per million (PPM) paramethoxyphenol added as an inhibitor to prevent polymerization of the ester and the toluene distilled off in vacuo. Final pressure was 28 inches of mercury, final temperature of the reaction mixture 100° C. The product was filtered, giving a clear yellow liquid having a viscosity of 17 cps. (25° C. Brookfield viscometer), a hydroxyl number of 10 maximum, an acid number of 0.5 and a gardner color of 1.

EXAMPLE II

Preparation of the Diacrylate of Propoxylated Neopentyl Glycol with a Degree of Propoxylation of 2

(A) 44.8 grams of neopentyl glycol were charged to a reaction flask equipped as described in Example I A above, and reacted with 55 grams of propylene oxide and 0.2 gram caustic potash under the conditions described in Example I A above until the final mixture was a clear light liquid with a hydroxyl number of 483–490 and a gardner color of 2.

(B) 67.05 grams of the propoxylated neopentyl glycol with a degree of propoxylation of 2 prepared in part A above were azeotropically esterified with 45.8 grams of acrylic acid in accordance with the procedure of Example I B. The final mixture was a clear yellow liquid having a gardner color of 3, a viscosity of 22 cps. (Brookfield viscometer at 25° C.), an acid number less than 0.5 and a maximum hydroxyl number of 20.

EXAMPLE III (A) Preparation of ethoxylated tripropylene glycol with a degree of ethoxylation of 2.

0.1 gram caustic potash was added to 68.5 grams of tripropylene glycol in a reaction flask equipped as described in Example I A above. The mixture was heated to 130°–140° C. where the mixture was evacuated under pressure to remove any water. Then 31.4 grams of ethylene oxide was slowly introduced. On completion the reaction was cooled. The final mixture was a clear liquid with a Gardner color of 2. It had a hydroxyl number of 390–400.

(B) Preparation of the diacrylate of the ethoxylated tripropylene glycol obtained in accordance with part A.

70 grams of the ethoxylated tripropylene glycol with a degree of ethoxylation of 2 obtained in accordance with part A above were azeotropically esterified with 39.7 grams acrylic acid in 32.5 grams of toluene in the presence of 2.4 grams p-toluene sulphonic acid and inhibitors, until no more water could be isolated. On completion, the product was washed and neutralized with sodium carbonate and the toluene distilled off as described in Example I, part B. The final mixture was a clear yellow liquid with a hydroxyl number of 10 maximum, viscosity of less than 100 cps. (Brookfield viscometer at 25° C.) and an acid number of 0.5.

EXAMPLE IV

Production of the Diacrylate of an Ethoxylated Tripropylene Glycol with a Degree of Ethoxylation of 4

(A) 236 grams of tripropylene glycol were charged along with 0.3 gram caustic potash into a reaction flask equipped as described in Example I, part A and the mixture was reacted with 220 grams of ethylene oxide to obtain a degree of ethoxylation of 4 in accordance with the procedure of Example III A. On completion, the mixture was a clear liquid with a hydroxyl number of 300–310.

(B) 350 grams of the ethoxylated tripropylene glycol with a degree of ethoxylation of 4 of part A above, was azeotropically esterified with 150 grams of acrylic acid and 10.2 grams p-toluene sulphonic acid in 157 grams toluene as described in Example III, part B. The final mixture was a clear yellow liquid with a viscosity of less than 40 cps. (Brookfield viscometer at 25° C.) and a maximum hydroxyl number of 10.

EXAMPLE V (A) Production of ethoxylated 1,6-hexanediol with a degree of ethoxylation of 2.

426 grams of 1,6-hexanediol was charged to a reaction flask as described in Example I A above. The flask was heated to 60°–70° C. where 0.6 gram caustic potash was added, then heated to and evacuated at 100° C. Then 318 grams of ethylene oxide were added slowly at 125°–130° C. until the addition was completed and then cooled. The final product was a slightly hazy colorless liquid with a hydroxyl number of 530–540.

(B) Production of the diacrylate of an ethoxylated 1,6-hexanediol with a degree of ethoxylation of 2.

585 grams of the ethoxylated 1,6-hexanediol with a degree of ethoxylation of 2 obtained in part A above were azeotropically esterified with 420 grams acrylic acid in 331 grams of toluene in the presence of 26 grams p-toluene sulphonic acid and inhibitors until no more water could be isolated. On completion, the product was washed and neutralized with sodium carbonate and the toluene was distilled off following the procedure of Example I B. The final mixture was a clear yellow liquid with a hydroxyl number of less than 11, a viscosity of 18 cps. (Brookfield viscometer at 25° C.) and a gardner color of less than 4.

The data appearing in the following Table are based upon tests using the diluents whose preparations are described above as well as using diluents whose preparations, although not described, utilized the same method of preparation as those described. For purpose of comparison, data relating to use of the diacrylates of 1,6-hexanediol, neopentyl glycol and tripropylene glycol are included.

TABLE

| Product | Cure Rate No. of Passes Paper | Cure Rate No. of Passes Alum. | Cure Rate No. of Passes Tin | Elongation (%) | Tensile Strength (lbs./sq.in.) | Solvent Resistance (No. of Rubs) Paper | Solvent Resistance (No. of Rubs) Alum. | Solvent Resistance (No. of Rubs) Tin | Draize (PII) | Scuff Resistance Paper | Scuff Resistance Alum. | Scuff Resistance Tin | Adhesion Paper | Adhesion Alum. | Adhesion Tin |
|---|---|---|---|---|---|---|---|---|---|---|---|---|---|---|---|
| 1,6-hexane diol diacrylate | 15 | 15 | 15 | Brittle Film | Brittle Film | 100 | 15 | 10 | 3-4 | P | P | P | E | E | F |
| 1,6-hexane diol(3.7 moles propylene oxide) diacrylate | 10 | 10 | 10 | — | — | 15 | 8 | 4 | 2 | F | F | F | E | E | G |
| 1,6-hexane diol (2 moles ethylene oxide) diacrylate | 10 | 10 | 10 | 3 | 542 | 44 | 54 | 20 | — | G | G | G | E | F | F |
| Neopentyl glycol diacrylate | 20 | 20 | 20 | Brittle Film | Brittle Film | 25 | 70 | 20 | 3-5 | F | F | F | E | G | F |
| Neopentyl glycol (2 moles ethylene oxide) diacrylate | 18 | 20 | 20 | 3 | 1236 | 100 | 76 | 55 | 0.9-4.3 | G | G | G | E | F | F |
| Neopentyl glycol (4 moles ethylene oxide) diacrylate | 10 | 10 | 10 | — | — | 23 | 8 | 9 | 4.3 | G | G | G | E | G | F |
| Neopentyl glycol (6 moles ethylene oxide) diacrylate | 8 | 8 | 8 | — | — | 8 | 8 | 8 | 3.2 | G | G | G | E | F | F |
| Neopentyl glycol (2 moles propylene oxide) diacrylate | 18 | 20 | 20 | 6 | 784 | 100 | 32 | 30 | 0.85-2.0 | F | G | G | E | F | F |
| Neopentyl glycol (4 moles propylene oxide) diacrylate | 15 | 15 | 15 | — | — | 9 | 9 | 9 | 2.2 | G | G | G | G | G | G |
| Tripropylene glycol diacrylate | 15 | 15 | 15 | 2 | 3269 | 17 | 15 | 13 | 3.0-3.8 | P | P | P | G | F | F |
| Tripropylene glycol (2 moles ethylene oxide) diacrylate | 10 | 10 | 10 | 3 | 434 | 40 | 15 | 11 | — | G | G | G | E | F | F |
| Tripropylene glycol (4 moles ethylene oxide) diacrylate | 3 | 3 | 4 | 2 | 216 | 4 | 4 | 4 | — | G | G | G | E | E | F |

As the data in the Table indicate, no single diluent is superior in all instances when compared with its non-alkoxylated counterpart. However, each diluent has a faster cure rate and improved scuff resistance than its non-alkoxylated counterpart. Moreover, the diacrylate of neopentyl glycol ethoxylated with 2 moles of ethylene oxide is considerably superior to the diacrylate of neopentyl glycol in the properties of percent elongation, tensile strength, solvent resistance, Draize and scuff resistance. The other products demonstrate a selective superiority as shown by improvements over their non-alkoxylated counterparts in specific properties.

In addition to the previously described skin irritation data, the following toxicological data is set forth for the product of Example II, i.e., the diacrylate of the adduct of neopentyl glycol and two moles of propylene oxide. For comparison purposes, toxicological data for neopentyl glycol diacrylate is also set forth.

| Test | Neopentyl Glycol (2 Moles Propylene Oxide) Diacrylate | Neopentyl Glycol Diacrylate |
| --- | --- | --- |
| Eye irritation (rabbit) unwashed eyes | A Draize score of 2.3 out of a possible 110 (recovery in 7 days)-minimal eye irritant | Definite eye irritant |
| Dermal LD$_{50}$ (rabbit) | >5000 mg/kg | 0.283 ml/kg (approx. 300 mg/kg) |
| Oral LD$_{50}$ (rat) | >10000 mg/kg | 5.19 ml/kg (approx. 5700 mg/kg) |
| Mutagenicity (Ames) | Negative | Negative |

A product, the diacrylate of the reaction product of neopentyl glycol with two moles of propylene oxide, was analyzed by gas chromotography for distribution of the propoxylate portion of the diacrylate using a Hewlett Packard 5830 A equipped with a flame detector using a SE 30 column. The product was prepared in accordance with the procedure of Example II, above. All percents are percent by volume.

| Component | % by Vol. |
| --- | --- |
| Dipropylene glycol | 13.9 |
| Tripropylene glycol | 2.4 |
| Monopropoxylate | 12.4 |
| Dipropoxylate | 41.4 |
| Tripropoxylate | 10.5 |
| Tetrapropoxylate | 5.8 |
| Pentapropoxylate | 5.5 |
| Hexapropoxylate | 1.0 |

While the invention has been described with reference to certain specific embodiments thereof it is understood that it is not to be so limited since alterations and changes may be made therein which are within the full intended scope of the appended claims.

What is claimed is:

1. Diacrylates of the reaction product of neopentyl glycol with from about 2 to about 6 moles of ethylene oxide.

2. Diacrylates of the reaction product of neopentyl glycol with from about 2 to about 4 moles of propylene oxide.

3. The diacrylate of claim 1 wherein the reaction product is the reaction product of neopentyl glycol and about 2 moles of ethylene oxide.

4. The diacrylate of claim 1 wherein the reaction product is the reaction product of neopentyl glycol and about 4 moles of ethylene oxide.

5. The diacrylate of claim 1 wherein the reaction product is the reaction product of neopentyl glycol and about 6 moles of ethylene oxide.

6. The diacrylate of claim 2 wherein the reaction product is the reaction product of neopentyl glycol and about 2 moles of propylene oxide.

7. The diacrylate of claim 2 wherein the reaction product is the reaction product of neopentyl glycol and about 4 moles of propylene oxide.

8. A radiation-hardenable composition comprising a radiation-hardenable oligomer and a radiation-hardenable diluent which is a diacrylate of the reaction product of neopentyl glycol with from about 2 to about 6 moles of ethylene oxide.

9. A radiation-hardenable composition comprising a radiation-hardenable oligomer and a radiation-hardenable diluent which is a diacrylate of the reaction product of neopentyl glycol with from about 2 to about 4 moles of propylene oxide.

10. The composition of claim 8 wherein said diluent is the diacrylate of the reaction product of neopentyl glycol and about 2 moles of ethylene oxide.

11. The composition of claim 8 wherein said diluent is the diacrylate of the reaction product of neopentyl glycol and about 4 moles of ethylene oxide.

12. The composition of claim 8 wherein said diluent is the diacrylate of the reaction product of neopentyl glycol and about 6 moles of ethylene oxide.

13. The composition of claim 9 wherein said diluent is the diacrylate of the reaction product of neopentyl glycol and about 2 moles of propylene oxide.

14. The composition of claim 9 wherein said diluent is the diacrylate of the reaction product of neopentyl glycol and about 4 moles of propylene oxide.

15. The composition of claim 8 wherein said diluent is present in an amount of from about 5% to about 80% by weight of the composition.

16. The composition of claim 9 wherein said diluent is present in an amount of from about 5% to about 80% by weight of the composition.

* * * * *

UNITED STATES PATENT AND TRADEMARK OFFICE
Certificate

Patent No. 4,382,135                                       Patented May 3, 1983

On petition requesting issuance of a certificate for correction of inventorship pursuant to 35 USC 256, it has been found that the above-identified patent, through error and without any deceptive intent, improperly sets forth the inventorship. Accordingly, it is hereby certified that the correct inventorship of this patent is Joseph V. Sinka, Francis A. Higbie, James F. Hern and Edward J. Gleason.

Signed and Sealed this 2nd Day of September, 1986.

BRADLEY R. GARRIS,
*Office of the Deputy Assistant Commissioner for Patents.*